United States Patent [19]

Hakenewerth et al.

[11] Patent Number: 4,684,802
[45] Date of Patent: Aug. 4, 1987

[54] ELLIPTICAL FINGER PRESS SCANNER WITH ROTATING LIGHT SOURCE

[75] Inventors: Paul A. Hakenewerth; Aspi B. Wadia, both of Charlotte, N.C.; James R. Walker, Longmont, Colo.; James M. White, Charlotte, N.C.

[73] Assignee: International Business Machines Corporation, Armonk, N.Y.

[21] Appl. No.: 830,650

[22] Filed: Feb. 18, 1986

[51] Int. Cl.$^4$ .......................... H01J 3/14; G06K 9/00
[52] U.S. Cl. ................................... 250/235; 250/556; 356/71; 382/4
[58] Field of Search .................. 356/71; 250/235, 236, 250/556; 382/4, 5

[56] References Cited

U.S. PATENT DOCUMENTS 4,120,585 10/1978 DePalma ............................. 356/71
4,340,300 7/1982 Ruell ................................... 356/71

OTHER PUBLICATIONS

Fingertip Orienting and Ridge Viewing Apparatus, IBM Technical Disclosure Bulletin, vol. 8, No. 3, dated Aug. 1965, p. 435.

*Primary Examiner*—Edward P. Westin
*Assistant Examiner*—Jessica L. Ruoff
*Attorney, Agent, or Firm*—Karl O. Hesse; Donald F. Voss

[57] ABSTRACT

A scanner for scanning an increased area of a finger held or pressed on a concave elliptically cylindrical surface having two focal axes includes a linear light source positioned at one focal axis of a first reflective cylindrical elliptical surface, the other focal axis coinciding with one focal axis of the concave elliptical surface in contact with the finger. A second reflective, cylindrical elliptical surface has two focal axes where one of the axes coincides with the position of a linear array combination of photosensitive elements and charged coupled devices and the other coincides with the other focal axis of the concave elliptical surface in contact with the finger. The linear light source resides within a scanning drum having a longitudinal opening or slit and suitable rotated whereby a line of light is projected along the cylindrical elliptical surface of the first reflective surface whereby light rays are reflected to the finger contact surface to scan a finger held thereon and then totally internally reflected to the second reflective surface and then reflected therefrom as an image on the linear array.

15 Claims, 2 Drawing Figures

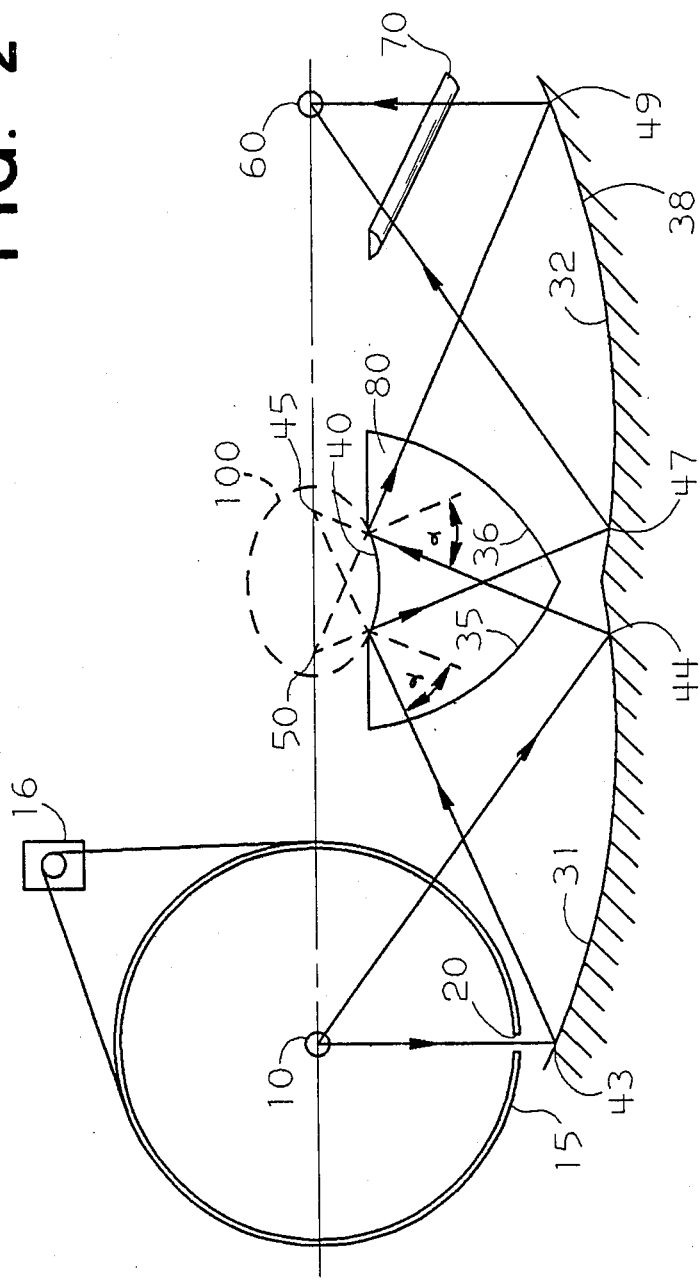

ELLIPTICAL FINGER PRESS SCANNER WITH ROTATING LIGHT SOURCE

TECHNICAL FIELD

This invention relates to fingerprint minutiae verification systems and more particularly to such systems where the finger of a person is pressed or held in contact with an optical surface and still more particularly to such systems where the finger is pressed on a concave surface which is scanned with a scanner system to provide input into a recognition or image processing system.

BACKGROUND ART

Fingerprint verification systems for personal identification include ones where a latent finger pattern is formed first and then scanned and ones where the finger print pattern is scanned while the finger is held in a pressed position against an optical surface. In the latter systems some have a flat finger contact surface which limits the scanning area and is subject to variations or distortions of the minutiae depending upon finger pressure. Other such systems use a deformable contact surface such as in U.S. Pat. Nos. 4,120,585 and 4,340,300 to increase the area of contact and still other systems use a contact surface having a shallow elliptic indentation as set forth in the IBM Technical Disclosure Bulletin Vol. 8 No. 3 dated August 1965 page 435 entitled "Fingertip Orienting and Ridge Viewing Apparatus". Although the contact area is increased when using a concave depression, the light rays reflected off the curved surface tend to diverge and undergo refraction. Additionally the image focuses on a curve. Also, because parallel light rays impinge upon a curved surface at different angles, there is not total internal reflection of all parallel incident light rays and consequently the image area is reduced with previous systems. The present invention results in an increased image area even though the finger contact surface is a cylindrical elliptical surface.

SUMMARY OF THE INVENTION

The principal object of the present invention is to provide an improved fingerprint minutiae verification system and more particularly to provide such a system which includes a cylindrical elliptical finger contact surface and scanning system whereby an increased image area results.

These objects are achieved by locating a light source at one focal axis of a first reflective cylindrical elliptical surface which has a second focal axis coinciding with one of two focal axis of said cylindrical elliptical finger contact surface. A second reflective cylindrical elliptical surface has one focal axis coinciding with the position of a photo detector and another focal axis coinciding with another focal axis of the cylindrical elliptical finger contact surface. The light source is caused to scan across the first reflective surface.

BRIEF DESCRIPTION OF THE DRAWINGS

FIG. 2 is a schematic diagram illustrating an alternate embodiment of the invention.

DETAILED DESCRIPTION

Figure 1:
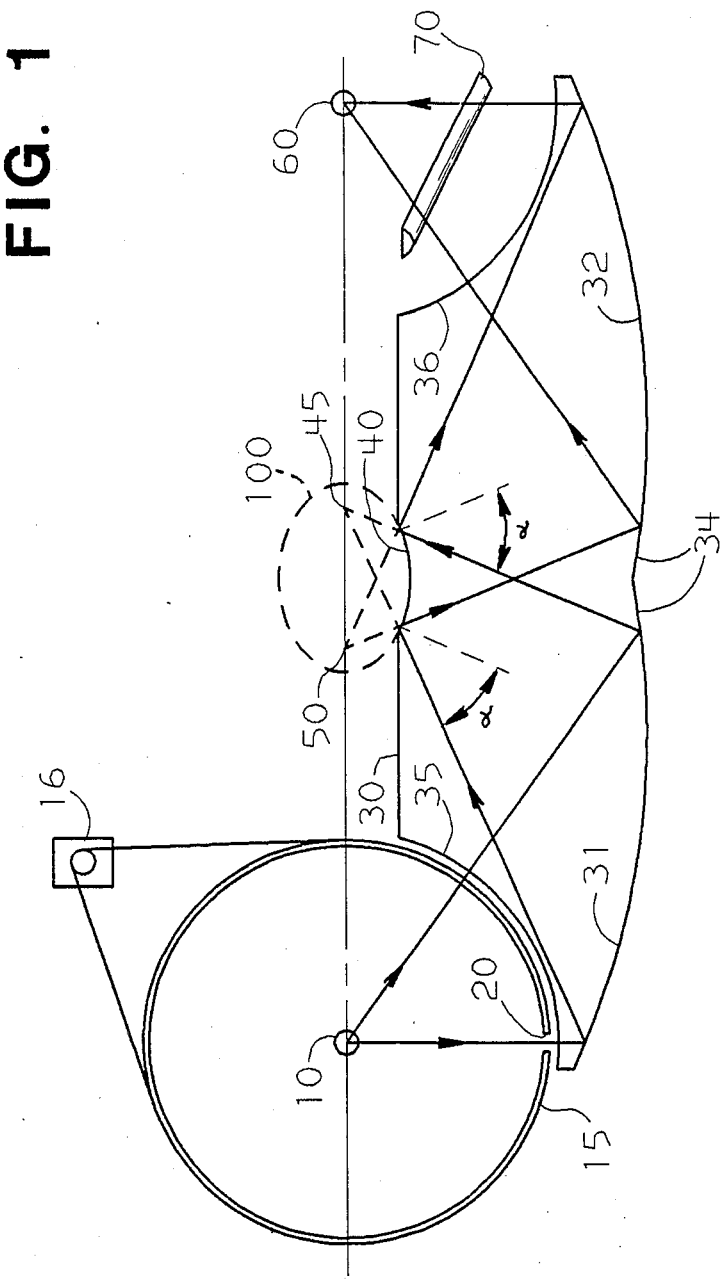
FIG. 1 is a schematic diagram illustrating a preferred embodiment of the invention.

With reference to the drawings and particularly to FIG. 1, the invention is illustrated by way of example as including linear light source 10 positioned within scanning cylinder or drum 15 having a longitudinal slot 20 in its peripheral surface. The light source 10 is mounted at the center of the drum 15 and also at the center of curvature of arcuate cylindrical surface 35 of optical element 30. This arcuate surface 35 provides an orthogonal entrance area into element 30 for light rays coming from light source 10 and passed by slot 20 as drum 15 is rotated by drive 16.

Light source 10 is at one focal axis of cylindrical elliptical reflective surface 31 of optical element 30. By this arrangement rays of light from light source 10 scanned onto surface 31 as drum 15 rotates are reflected to pass to one focal axis 45 of cylindrical elliptical finger contact surface 40 of element 30. The incident light rays from light source 10 are normal to the arcuate surface 35 and thus there is no refraction of light at this surface.

Because the elliptical surface 40, in this example is an arcuate surface centered at the minor axis of an approximately 45 degree ellipse, the rays of light reflected off surface 31 make an angle of incidence alpha that lies between 43 degrees and 45 degrees. Prism 30 is made of glass or plastic which has a refractive index such that the glass to air medium has a critical angle of reflection of approximately 42 degrees reflection. When a person places a finger 100 in contact with surface 40, only the ridges of the finger touch that surface. Surface 40 thus presents to the incident rays of light a glass to air medium at the valleys of the finger print and glass to skin medium at the ridges. The rays that are incident on surface 40 at the valleys will be totally internally reflected and those at the ridges will be absorbed. Thus there is high contrast between ridges and valleys. The light rays reflected internally off surface 40 appear to come from the focal point 50 and are reflected to impinge upon reflective surface 32 of element 30. The light rays are reflected by cylindrical elliptical surface 32 of element 30. The light rays are reflected by cylindrical elliptical surface 32 to exit element 30 through an arcuate circularly cylindrical exit surface 36. Exit surface 36 has a curvature centered about a light detector 60 consisting of a linear array of light sensing elements read out by charge coupled devices (CCD). The light rays reflected by surface 32 are normal to circularly cylindrical arcuate exit surface 36 and thus leave element 30 unrefracted.

In the plane orthogonal to the projection shown in FIG. 1, the reflected light rays exiting element 30 are focused onto the array 60 by cylindrical lens system 70 which is orthogonal to the axis of array 60. A lens system is not needed between light source 10 and entry surface area 35 because it is desirable for the light to focus transversely on this surface area in order to produce ridge-valley image portions of the finger 100 pressed at surface 40.

Optical element 30 is relatively simple to manufacture and preferably is molded and the reflective surfaces 31 and 32 are formed by applying silver or other highly reflective coatings on the exterior portion 34 of element 30. Element 30 is made from optical quality glass or plastic with an index of refraction of typical values which normally cause total internal reflection of light rays impinging upon the surface at angles alpha between 43 degrees and 45 degrees.

In an alternate embodiment of the invention, illustrated by way of example in FIG. 2 where like or equivalent elements have the same reference characters as in FIG. 1. Light source 10 is positioned within drum 15 to be at one focal axis of elliptical cylindrical reflective surface 31 of mirror 38. The other focal axis of surface 31 coincides with one focal axis 45 of elliptical cylindrical surface 40 of prism 80. Light rays from light source 10 impinge upon reflective surface 31 as they pass through slot 20 as drum 15 rotates. The light rays reflected by surface 31 enter prism 80 through an arcuate circularly cylindrical surface 35 thereof which is centered about or has its axis at focal point 45. Thus the reflected light rays enter prism 80 normal to surface 35 in the projection view of FIG. 2. These light rays entering prism 80 strike elliptical finger contact surface 40 of prism 80 and are totally internally reflected except where fingerprint ridges contact the surface to exit prism 80 through arcuate circularly cylindrical surface 36 which is centered about focal point 50. Focal points 45 and 50 are also focal points of finger contact surface 40.

The light rays exiting prism 80 are unrefracted in the projected view of FIG. 2 and impinge upon elliptical reflective surface 32 of mirror 38 which has one focal axis coinciding with focal axis 50 and another one coinciding with the position of sensor array 60. It should be noted that reflective surfaces 31 and 32 are illustrated as being surfaces of a single mirror 38. There could be separate mirrors for each reflective surface without departing from the invention.

The elliptical finger contact surface 40 in FIG. 2 is an arc centered at the minor axis of an ellipse. In both embodiments a person's finger 100 is pressed or held in contact with elliptical contact surface 40.

Light rays from light source 10 passing through slot 20 sweep along the surface area of reflective surface 31 starting at 43 and ending at 44 as drum 15 rotates. The light rays reflected from surface 31 sweep the contact surface 40 to illuminate the pressed finger 100. The light rays reflected internally from surface 40 sweep across reflective surface 32 from 47 to 49 and are reflected as an image focused upon sensor array 60. As in the case of the embodiment of FIG. 1, the fingerprint ridges absorb light rays impinging upon contact surface 40 and the fingerprint valleys reflect the impinging light rays and it is these reflected light rays that are reflected internally in prism 80 to exit surface 36 thereof and impinge upon reflective surface 32.

While the invention has been described with reference to preferred and alternate embodiments, it should be apparent that many changes can be made without departing from the scope of the invention which is to be construed by the following claims.

Having thus described the invention, what is claimed as new and desired to be secured by Letters Patent is:

1. A fingerprint scanner comprising:
   a cylindrical elliptically concave finger contact surface in a prism for receiving a finger to be scanned, the finger contact surface having a first focal axis and a second focal axis parallel to said first focal axis;
   a first cylindrically elliptical reflecting means having a source focal axis and a sink focal axis, the sink focal axis being the same as said second focal axis, and the source focal axis being parallel to and lying in the plane of said first and second focal axes;
   a scanning light source located at said source focal axis of said first cylindrically elliptical reflecting means for scanning a line of light across reflecting means for reflecting the line of light onto said finger contact surface from where it is selectively reflected depending upon whether or not a ridge of a fingerprint is in contact with the finger contact surface at the point of possible reflection;
   a second cylindrically elliptical reflecting means having a sink focal axis and a source focal line, the source focal axis being the same as said first focal axis, and the sink focal axis being parallel to and lying in the plane of said first and second focal axes; and
   an array of light detectors located at said sink focal axis of said second cylindrically reflecting means for receiving light selectively reflected from the finger contact surface and again reflected from said second reflecting means.

2. The fingerprint scanner of claim 1 wherein said first and second reflecting means are convex surfaces in the prism containing said finger contact surface.

3. The fingerprint scanner of claim 1 wherein said first and second reflecting means are concave mirror surfaces and where the prism finger contact surface further comprises:
   a cylindrical surface which is normal to the light reflected from said first reflecting means to said finger contact surface; and
   a cylindrical surface which is normal to the light reflected from said finger contact surface to said second reflecting means.

4. A finger press scanner comprising:
   light source means for sweeping light rays progressively along an arcuate path,
   an optical finger contact surface for supporting a finger to be scanned, said finger contact surface being elliptical and having first and second focal axes for total internal reflection of light rays;
   a first elliptical reflective surface positioned to receive light rays from said light source means and reflect the same to said finger contact surface to scan a finger placed thereon, said finger contact surface internally reflecting only those light rays reflected by said first elliptical reflective surface unabsorbed by fingerprint valleys;
   light sensing means; and
   a second elliptical reflective surface positioned to receive light rays internally reflected by said finger contact surface and reflecting the same to said light sensing means whereby said sensing means produces data signals indicating detection of fingerprint valleys in response to the presence of internally reflected light rays and indicating detection of fingerprint ridges in response to the absence of internally reflected light rays.

5. The finger press scanner of claim 4 wherein said light source means comprises:
   a linear light source positioned at one focal axis of said first elliptical reflective surface, and
   a rotating drum concentrically positioned about said linear light source and having a longitudinal slot for passing light rays from said linear light source.

6. The finger press scanner of claim 4 wherein said first elliptical reflective surface has a focal axis coinciding with the first focal axis of said optical finger contact surface.

7. The finger press scanner of claim 4 wherein said light sensing means is a linear array combination of photosensitive elements and charge coupled devices located a predetermined position.

8. The finger press scanner of claim 4 wherein said second elliptical reflective surface has a focal axis coinciding with the second focal axis of said finger contact surface.

9. The finger press scanner of claim 7 wherein said second elliptical reflective surface has a focal axis coinciding with the predetermined position of said linear array of charge coupled devices.

10. The finger press scanner of claim 4 wherein said finger contact surface is an elliptically cylindrical surface centered at the minor axis of an ellipse.

11. The finger press scanner of claim 10 wherein said ellipse is a 45 degree ellipse.

12. The finger press scanner of claim 5 wherein said finger contact surface, and said first and second elliptical reflective surfaces are integral surfaces of a unitary optical element.

13. The finger press scanner of claim 12 wherein said unitary optical element further comprises:

a first arcuate surface formed to confront said drum and receive light rays normally passed through said slot, and a second arcuate surface for passing light rays reflected by said second elliptical reflective surface.

14. The finger press scanner of claim 7 further comprising:

cylindrical lens means positioned to receive light rays reflected by said second elliptical reflective surface and focus the same upon said linear array combination of photosensitive elements and charge coupled devices.

15. The finger press scanner of claim 4 wherein said optical finger contact surface is formed in a prism having a first arcuate surface for receiving normally light rays reflected by said first elliptical reflective surface and pass the same to said finger contact surface and a second arcuate surface for normally receiving light rays internally reflected by said finger contact surface and pass the same to said second elliptical reflective surface.

* * * * *